US012150905B2

(12) United States Patent
Theunick et al.

(10) Patent No.: US 12,150,905 B2
(45) Date of Patent: Nov. 26, 2024

(54) PATIENT SUPPORT APPARATUS WITH NOTIFICATION SYSTEM

(71) Applicant: Stryker Corporation, Kalamazoo, MI (US)

(72) Inventors: Christopher R. Theunick, Mattawan, MI (US); Brianna R. Graves, Kalamazoo, MI (US); Martin Fecteau, Redmond, WA (US); Annie Désaulniers, Redmond, WA (US)

(73) Assignee: Stryker Corporation, Portage, MI (US)

( * ) Notice: Subject to any disclaimer, the term of this patent is extended or adjusted under 35 U.S.C. 154(b) by 1132 days.

(21) Appl. No.: 16/691,062

(22) Filed: Nov. 21, 2019

(65) Prior Publication Data

US 2020/0163818 A1    May 28, 2020

Related U.S. Application Data

(60) Provisional application No. 62/771,758, filed on Nov. 27, 2018.

(51) Int. Cl.
*A61G 7/057* (2006.01)
*A47C 27/08* (2006.01)

(52) U.S. Cl.
CPC ........ *A61G 7/05776* (2013.01); *A47C 27/082* (2013.01); *A61G 7/05769* (2013.01);
(Continued)

(58) Field of Classification Search
CPC ............ A61G 7/05776; A61G 7/05769; A61G 2203/20; A61G 2203/32; A61G 2203/34;
(Continued)

(56) References Cited

U.S. PATENT DOCUMENTS 4,751,754 A    6/1988  Bailey et al.
4,935,968 A    6/1990  Hunt et al.
(Continued)

FOREIGN PATENT DOCUMENTS

AU    2007203638 A1 *  2/2008  ............ A61G 7/015
EP       1884224 A2 *  2/2008  ............ A61G 7/015
(Continued)

*Primary Examiner* — Robert G Santos
(74) *Attorney, Agent, or Firm* — Warner Norcross + Judd LLP

(57) ABSTRACT

A patient support apparatus for supporting a patient includes a mattress with an inflatable mattress portion with a plurality of states. The apparatus further includes a control system to control inflation or deflation of the mattress portion to change its state between two or more of the states. The apparatus further includes a user interface in communication with the control system, which is configured to allow a user to select an inflate or deflate function of the mattress portion to change the state of the mattress portion. Further, the control system is operable to inflate or deflate the mattress portion in response to the signal being generated when a user selects an inflate or deflate function at the user interface. The control system is configured to generate a notification indicative of the selected state of the mattress portion to remind to a caregiver to change the selected state.

20 Claims, 13 Drawing Sheets

(52) U.S. Cl.
CPC ........ *A47C 27/081* (2013.01); *A61G 2203/20* (2013.01); *A61G 2203/32* (2013.01); *A61G 2203/34* (2013.01); *A61G 2203/44* (2013.01); *A61G 2210/00* (2013.01)

(58) Field of Classification Search
CPC ................. A61G 2203/44; A61G 2210/00; A47C 27/08; A47C 27/081; A47C 27/082; A47C 27/083
USPC ................. 5/713, 710, 706, 655.3, 654, 644
See application file for complete search history.

(56) References Cited

U.S. PATENT DOCUMENTS

| | | | |
|---|---|---|---|
| 4,953,243 A | 9/1990 | Birkmann | |
| 5,005,240 A | 4/1991 | Vrzalik | |
| 5,251,349 A | 10/1993 | Thomas et al. | |
| 5,375,273 A * | 12/1994 | Bodine, Jr. | A61G 7/001 5/710 |
| 5,542,136 A | 8/1996 | Tappel | |
| 5,560,057 A | 10/1996 | Madsen et al. | |
| 5,611,096 A | 3/1997 | Bartlett et al. | |
| 5,647,079 A | 7/1997 | Hakamiun et al. | |
| 5,920,934 A | 7/1999 | Hannagan et al. | |
| 6,061,855 A | 5/2000 | Flick | |
| 6,505,368 B1 | 1/2003 | Ellis et al. | |
| 6,591,437 B1 | 7/2003 | Phillips | |
| 6,820,640 B2 | 11/2004 | Hand et al. | |
| 7,055,195 B2 | 6/2006 | Roussy | |
| 7,225,488 B2 | 6/2007 | Wu | |
| 7,263,734 B1 | 9/2007 | Buchanan et al. | |
| 7,310,839 B2 | 12/2007 | Salvatini et al. | |
| 7,380,302 B2 | 6/2008 | Gilchrest, Jr. et al. | |
| 7,657,956 B2 * | 2/2010 | Stacy | A61G 7/05769 5/713 |
| 7,685,662 B2 | 3/2010 | Viard | |
| 7,810,195 B2 | 10/2010 | Biggie et al. | |
| 7,836,531 B2 | 11/2010 | Girard et al. | |
| 7,849,545 B2 | 12/2010 | Flocard et al. | |
| 8,108,957 B2 * | 2/2012 | Richards | A61H 23/04 5/734 |
| 8,397,326 B2 * | 3/2013 | Lafleche | A61G 7/05776 5/713 |
| 8,584,279 B2 * | 11/2013 | Richards | A61H 23/006 601/150 |
| 8,606,344 B2 * | 12/2013 | DiMaio | A61B 5/6887 600/407 |
| 8,777,879 B2 | 7/2014 | Johnson | |
| 8,799,011 B2 * | 8/2014 | Wilson | A61B 5/002 705/2 |
| 8,832,884 B2 * | 9/2014 | Stacy | A61G 7/05769 5/713 |
| 8,832,885 B2 * | 9/2014 | Lafleche | A61G 7/05761 5/713 |
| 8,856,992 B2 * | 10/2014 | Lafleche | A61G 7/05761 5/713 |
| 8,911,387 B2 | 12/2014 | Lafleche et al. | |
| 9,049,943 B2 | 6/2015 | Caminade et al. | |
| 9,211,019 B2 | 12/2015 | Driscoll, Jr. et al. | |
| 9,295,598 B2 | 3/2016 | Roussy et al. | |
| 9,566,202 B2 | 2/2017 | Chiang et al. | |
| 9,820,904 B2 * | 11/2017 | Lafleche | A61H 9/0078 |
| 10,098,798 B2 * | 10/2018 | Stacy | A61G 7/05769 |
| 10,130,539 B2 * | 11/2018 | Stacy | A61G 7/05792 |
| 10,258,538 B2 | 4/2019 | Barta et al. | |
| 10,376,214 B2 * | 8/2019 | Hayes | A61G 7/0509 |
| 10,507,147 B2 | 12/2019 | Bobey et al. | |
| 10,695,247 B2 * | 6/2020 | Wilson | A61G 7/05776 |
| 10,952,925 B2 | 3/2021 | Centen | |
| 11,033,233 B2 * | 6/2021 | Hayes | A61G 7/018 |
| 11,058,603 B2 | 7/2021 | Chen et al. | |
| 11,116,684 B2 | 9/2021 | Poulos et al. | |
| 2007/0169268 A1 | 7/2007 | Lemire et al. | |
| 2008/0028533 A1 * | 2/2008 | Stacy | A61G 7/015 5/713 |
| 2008/0109964 A1 | 5/2008 | Flocard et al. | |
| 2009/0013470 A1 * | 1/2009 | Richards | G16Z 99/00 5/613 |
| 2009/0144903 A1 | 6/2009 | Delvaux et al. | |
| 2009/0275808 A1 * | 11/2009 | DiMaio | A61B 6/56 128/845 |
| 2010/0132116 A1 * | 6/2010 | Stacy | A61G 7/0525 5/713 |
| 2011/0208541 A1 * | 8/2011 | Wilson | A61G 7/0527 705/2 |
| 2011/0289691 A1 * | 12/2011 | Lafleche | A47C 27/10 5/713 |
| 2011/0296623 A1 * | 12/2011 | Lafleche | A61G 7/05761 5/713 |
| 2011/0296624 A1 * | 12/2011 | Lafleche | A61G 7/05761 5/713 |
| 2011/0301516 A1 * | 12/2011 | Lafleche | A47C 27/10 5/713 |
| 2012/0016281 A1 * | 1/2012 | Richards | A61G 7/002 601/54 |
| 2013/0049966 A1 | 2/2013 | Penninger et al. | |
| 2013/0061396 A1 * | 3/2013 | Lafleche | A61H 23/04 5/706 |
| 2014/0013515 A1 * | 1/2014 | Richards | G16Z 99/00 5/715 |
| 2014/0090173 A1 * | 4/2014 | DiMaio | A61B 5/704 5/81.1 R |
| 2014/0343968 A1 * | 11/2014 | Wilson | G16H 10/60 705/3 |
| 2014/0352074 A1 * | 12/2014 | Stacy | A61G 7/015 5/713 |
| 2015/0000045 A1 * | 1/2015 | Lafleche | A47C 27/10 5/713 |
| 2016/0022218 A1 * | 1/2016 | Hayes | A61B 5/7275 600/595 |
| 2016/0058639 A1 | 3/2016 | Lacasse et al. | |
| 2016/0193095 A1 | 7/2016 | Roussy et al. | |
| 2017/0014289 A1 * | 1/2017 | Stacy | A61G 7/0525 |
| 2017/0065474 A1 | 3/2017 | Trepanier et al. | |
| 2019/0060146 A1 * | 2/2019 | Wilson | A61G 7/05776 |
| 2019/0350529 A1 * | 11/2019 | Hayes | A61B 5/1118 |
| 2020/0008993 A1 | 1/2020 | Poulos et al. | |
| 2020/0163818 A1 | 5/2020 | Theunick et al. | |
| 2020/0268163 A1 | 8/2020 | Duvert et al. | |
| 2020/0323717 A1 | 10/2020 | Zerhusen et al. | |
| 2021/0244589 A1 | 8/2021 | Gowda et al. | |
| 2021/0298682 A1 * | 9/2021 | Hayes | A61B 5/024 |
| 2023/0157912 A1 | 5/2023 | Thota et al. | |

FOREIGN PATENT DOCUMENTS

| | | | | |
|---|---|---|---|---|
| EP | 1975750 A2 * | 10/2008 | | A61G 7/018 |
| EP | 1997467 A2 * | 12/2008 | | A61G 7/002 |
| EP | 2208486 A2 * | 7/2010 | | A61G 7/015 |
| EP | 2279719 A2 * | 2/2011 | | A61G 7/015 |
| EP | 1884224 B1 * | 11/2011 | | A61G 7/015 |
| EP | 2437127 A1 * | 4/2012 | | A61G 7/018 |
| EP | 2439601 A1 * | 4/2012 | | A61G 7/018 |
| EP | 2505175 A1 * | 10/2012 | | A61G 7/002 |
| EP | 2208486 B1 * | 11/2012 | | A61G 7/015 |
| EP | 1997467 B1 * | 11/2013 | | A61G 7/002 |
| EP | 2279719 B1 * | 12/2013 | | A61G 7/015 |
| EP | 2439601 B1 * | 3/2020 | | A61G 7/018 |
| EP | 1975750 B1 * | 6/2020 | | A61G 7/018 |
| EP | 2437127 B1 * | 4/2021 | | A61G 7/018 |
| WO | 0215835 | 2/2002 | | |
| WO | 2004/021952 A2 | 3/2004 | | |
| WO | WO-2009065109 A1 * | 5/2009 | | A61B 5/447 |
| WO | WO-2009135081 A2 * | 11/2009 | | A61B 5/00 |
| WO | 2014149392 | 9/2014 | | |
| WO | WO-2014151577 A1 * | 9/2014 | | A61B 5/002 |
| WO | 2015128618 | 9/2015 | | |

* cited by examiner

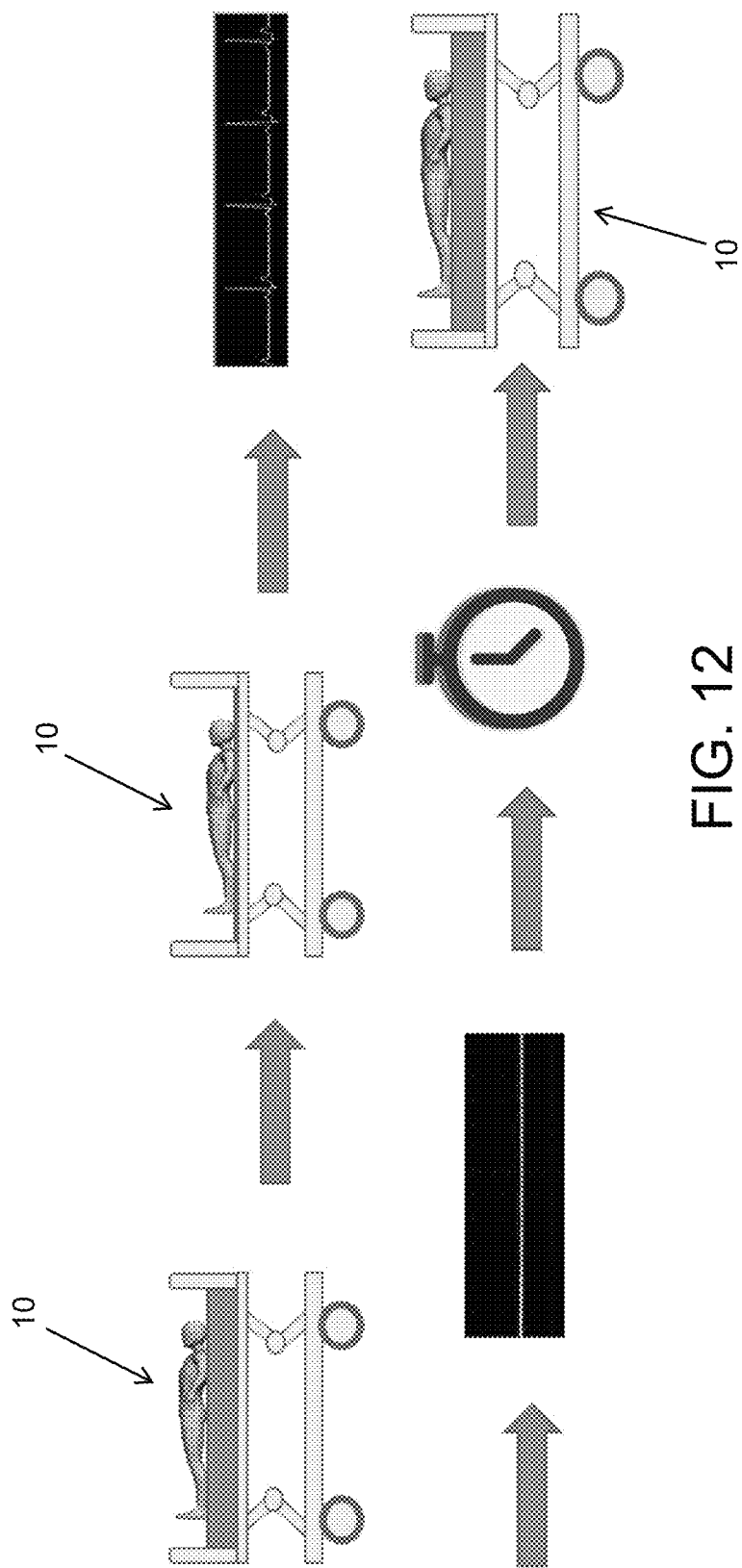

PATENT SUPPORT APPARATUS WITH NOTIFICATION SYSTEM

This application claims the benefit of U.S. Prov. Pat. Appl. Ser. No. 62/771,758, filed Nov. 27, 2018, by inventors Christopher R. Theunick et al. and entitled PATIENT SUPPORT APPARATUS WITH NOTIFICATION SYSTEM, which is incorporated by reference in its entirety herein.

TECHNICAL FIELD AND BACKGROUND

The present disclosure generally relates to a patient support apparatus, and more particularly to a patient support apparatus with a mattress and a notification system that notifies a caregiver about the status of the mattress, for example, when the mattress has been reconfigured to administer a treatment, such as cardiopulmonary resuscitation (CPR).

SUMMARY

The present disclosure provides a patient support apparatus with a mattress that has an inflatable mattress portion and a control system for controlling the inflation or deflation of the inflatable mattress portion.

In one embodiment, a patient support apparatus for supporting a patient includes a mattress with an inflatable mattress portion that has a plurality of states. The patient support apparatus further includes a control system configured to control inflation or deflation of the inflatable mattress portion to change the state of the inflatable mattress portion between two or more of the plurality of states. In addition, the patient support apparatus includes a user interface in communication with the control system, which is configured to allow a user to select an inflate or deflate function of the inflatable mattress portion to change the state of the inflatable mattress portion. Further, the control system is operable to inflate or deflate the inflatable mattress portion in response to the inflate or deflate signal being generated when a user selects an inflate or deflate function at the user interface. In addition, the control system is configured to generate a notification, which is indicative of the selected state of the inflatable mattress portion to provide a reminder to a caregiver to change the selected state of the inflatable mattress portion.

In one aspect, the selected state comprises a deflated state, and the control system generates the notification when the inflatable mattress portion is in the deflated state.

In another aspect, the control system comprises a pneumatic system with one or more fluid flow devices to inflate or deflate the inflatable mattress portion. For example, in one embodiment, the pneumatic system includes a CPR valve that is actuatable between a closed configuration where the flow of air from the inflatable mattress portion is blocked at the CPR valve, and an open position where the air can flow from the inflatable mattress portion to atmosphere through the CPR valve, for example, to allow the mattress to quickly deflate. Optionally, the CPR valve may be manually or electrically opened.

In one embodiment, the CPR valve may have an automatic reset mechanism so that after it is opened and the CPR treatment has been applied, the CPR valve can reset to its closed position.

In any of the above, the inflatable mattress portion comprises a plurality of bladders forming at least a portion of the patient support surface of the mattress, and optionally the entire patient support surface.

In any of the above apparatuses, the apparatus may also include a light assembly that is in communication with the control system, with the control system powering the light assembly to generate the notification.

In one aspect, the control system intermittently powers the light assembly to generate a flashing light with the light assembly when generating the notification.

In any of the above apparatuses, the user interface comprises a display, which is in communication with the control system, with the control system generating an icon at the display to generate the notification.

In any of the above apparatuses, alternately the user interface comprises a display, which is in communication with the control system and displays an icon, with the control system changing the icon at the display to generate the notification.

For example, in either case, the icon may be associated with the mattress.

In any of the above apparatuses, the user interface may comprise a touch screen display, which is in communication with the control system, with the control system generating a notification display window at the display to generate the notification.

For example, the display may generate a home screen (or a functional control template screen that allows a user to control one or more functions at the bed), with the notification display window covering at least a portion of the home screen (or the functional control template screen) for at least a preselected period of time.

In yet another aspect, the selected state of the inflatable mattress portion is a CPR state wherein the inflatable mattress portion is either fully deflated or inflated to a high pressure ("max inflate").

In yet another aspect, the notification display window includes an icon that when selected is an acknowledgement by a caregiver to the control system that the inflatable mattress portion is in the CPR state.

In addition, the notification display window may include an icon that when selected causes the control system to redirect a caregiver to a mattress control template screen where the caregiver can modify the selected state of the inflatable mattress portion.

In one embodiment, the notification display window includes an icon that when selected causes the control system to deactivate the CPR state of the inflatable mattress portion.

According to yet another embodiment, a patient support apparatus for supporting a patient includes a mattress, which includes an inflatable mattress portion with a plurality of states, and a control system configured to control inflation or deflation of the inflatable mattress portion to change between the states of the inflatable mattress portion. The apparatus further includes a user interface in communication with the control system. The user interface is configured to allow a user to input a selected state from the states of the inflatable mattress portion, with the control system being operable to inflate or deflate the inflatable mattress portion in response to the selected state input at the user interface. In addition, the control system is configured to automatically modify the selected state of the inflatable mattress portion in response to (1) a passage of time after the selected state was input into the control system or (2) a trigger, such as a sensed condition at the mattress.

In one aspect, the control system is configured to automatically modify the selected state of the inflatable mattress portion in response to a passage of time.

In any of the above apparatuses, the selected state of the inflatable mattress portion is a CPR state wherein the inflatable mattress portion is either fully deflated or inflated to a high pressure.

In one embodiment, the selected state of the inflatable mattress portion comprises a deflated state.

In other aspects, in any of the above apparatuses the inflatable mattress portion comprises a plurality of bladders forming at least a portion of the patient support surface.

In another aspect, the control system is configured to detect a characteristic associated with CPR. For example, the characteristic may comprise a force (including a force wave pattern) associated with CPR. Optionally, the control system automatically modifies the selected state of the inflatable portion of the mattress when the control system detects the force associated with CPR is no longer present. Further, the control system may automatically modify the selected state when the control system detects the force associated with CPR is no longer present after a period of time.

In another aspect, the characteristic comprises an increased weight on the mattress associated with CPR. For example, the control system may be configured to automatically modify the selected state when the increased weight is removed.

For example, in one embodiment, the control system includes at least one sensor, such as a load cell, to detect the increased weight.

In any of the above apparatuses, the control system is configured to monitor a condition, such as a biometric, of the patient supported thereon, and the sensed condition comprises detecting when the condition of the patient has changed.

For example, in one embodiment, the condition comprises a heart rate of the patient.

In another embodiment, the condition comprises a breathing rate of the patient.

According to yet another embodiment, a patient support apparatus includes a mattress with an inflatable mattress portion, which has a plurality of states, and a control system configured to control inflation or deflation of the inflatable mattress portion to change the state of the inflatable mattress portion between two or more of the plurality of states. The apparatus further includes a user interface in communication with the control system, which is configured to allow a user to select an inflate or deflate function of the inflatable mattress portion to change the state of the inflatable mattress portion. Further, the control system is operable to inflate or deflate the inflatable mattress portion in response to the inflate or deflate function being selected at the user interface.

In addition, the control system is configured to generate a notification to a device remote from the patient support apparatus, with the notification being indicative of the selected state of the inflatable mattress portion to provide a reminder to a caregiver to change the selected state of the inflatable mattress portion.

In one embodiment, the selected state of the inflatable mattress portion is a CPR state wherein the inflatable mattress portion is either fully deflated or inflated to a high pressure.

In one aspect, the inflatable mattress portion comprises a plurality of bladders forming at least a portion of the patient support surface, and optionally the entire patient support surface.

These and other objects, advantages, purposes, and features of the disclosure will become more apparent from the study of the following description taken in conjunction with the drawings.

DESCRIPTION OF THE FIGURES

FIG. 12 is a schematic drawing illustrating a CPR event at the patient support apparatus and an automated process for returning the mattress of the patient support apparatus to its pre-CPR event state;

DETAILED DESCRIPTION

Figure 1:
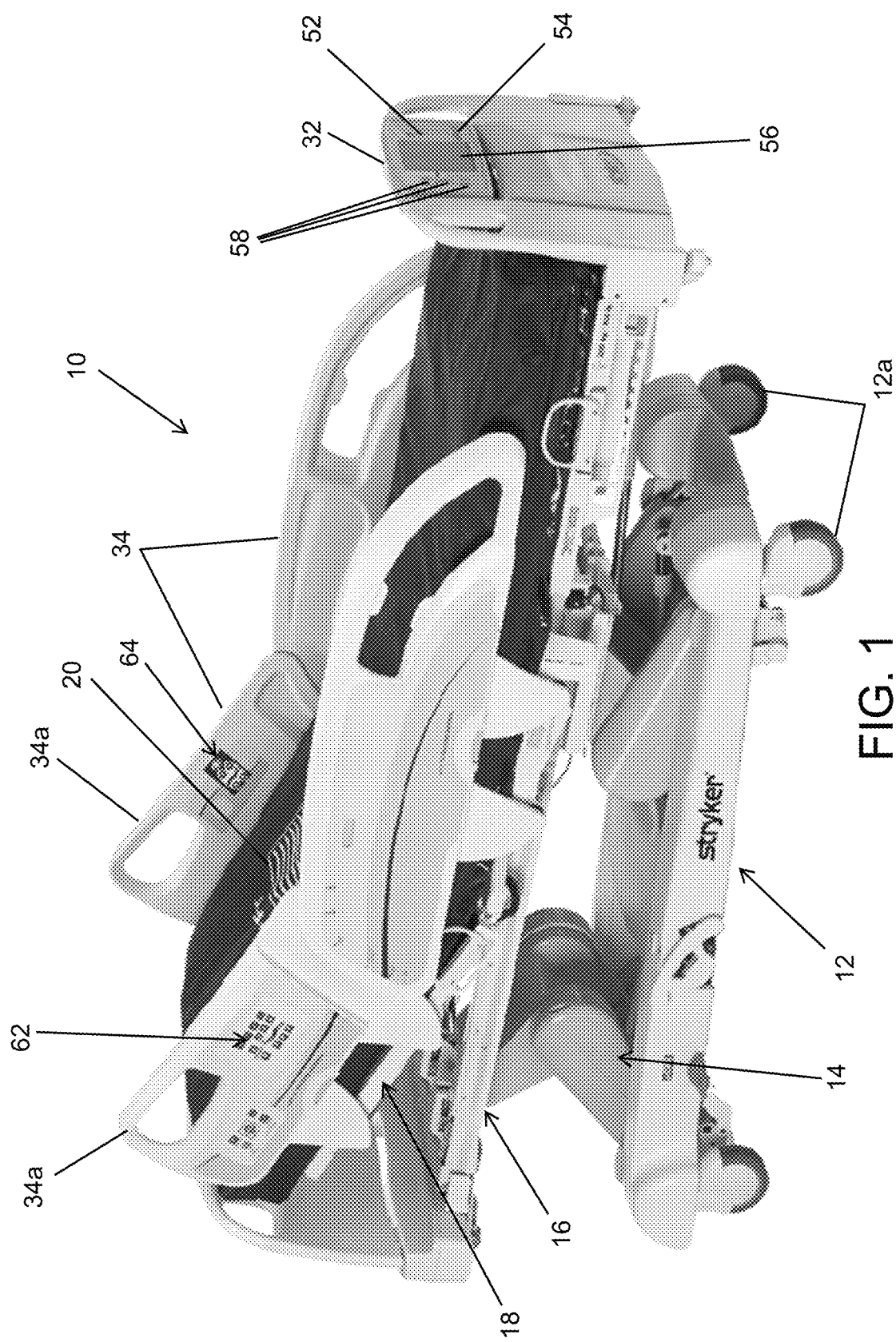
FIG. 1 is a perspective view of one embodiment of a patient support apparatus.

Referring to FIG. 1, the numeral 10 generally designates a patient support apparatus of the present disclosure. While described as a "patient" support apparatus, it should be understood that "patient" is to be construed broadly to include not only people undergoing medical treatment but also invalids and other persons, such as long-term care persons, who may need assistance or care but who may or may not be undergoing medical treatment. Further, although the particular form of patient support apparatus 10 illustrated in FIGS. 1 and 2 is a bed adapted for use in a hospital or other medical setting, it will be understood that patient support apparatus 10 could, in different embodiments, be a cot, a stretcher, a recliner, a wheelchair, or any other mobile structure capable of supporting a patient in a healthcare environment.

As will be more fully described below, patient support apparatus 10 provides support to a patient's body and, further, includes a mattress that has a plurality of states and a notification system to notify a caregiver when the caregiver should change the state of the mattress, for example from a treatment state to a pre-treatment state or vice versa. This is particularly suitable for a CPR event when the mattress is either deflated (where the patient bottoms out onto the underlying deck) or inflated to a maximum inflation state (where the mattress is very firm or substantially rigid) so that CPR can be administered, and then needs to be returned to its pre-CPR event state or another state. This may also be suitable, for example, when the mattress has been configured to deeply immerse a patient, for example an unconscious patient, in the mattress, but which immersion may not be suitable when the patient is conscious. In either example, it is or may be beneficial to notify a caregiver to return the mattress to its pre-treatment state.

Figure 2:
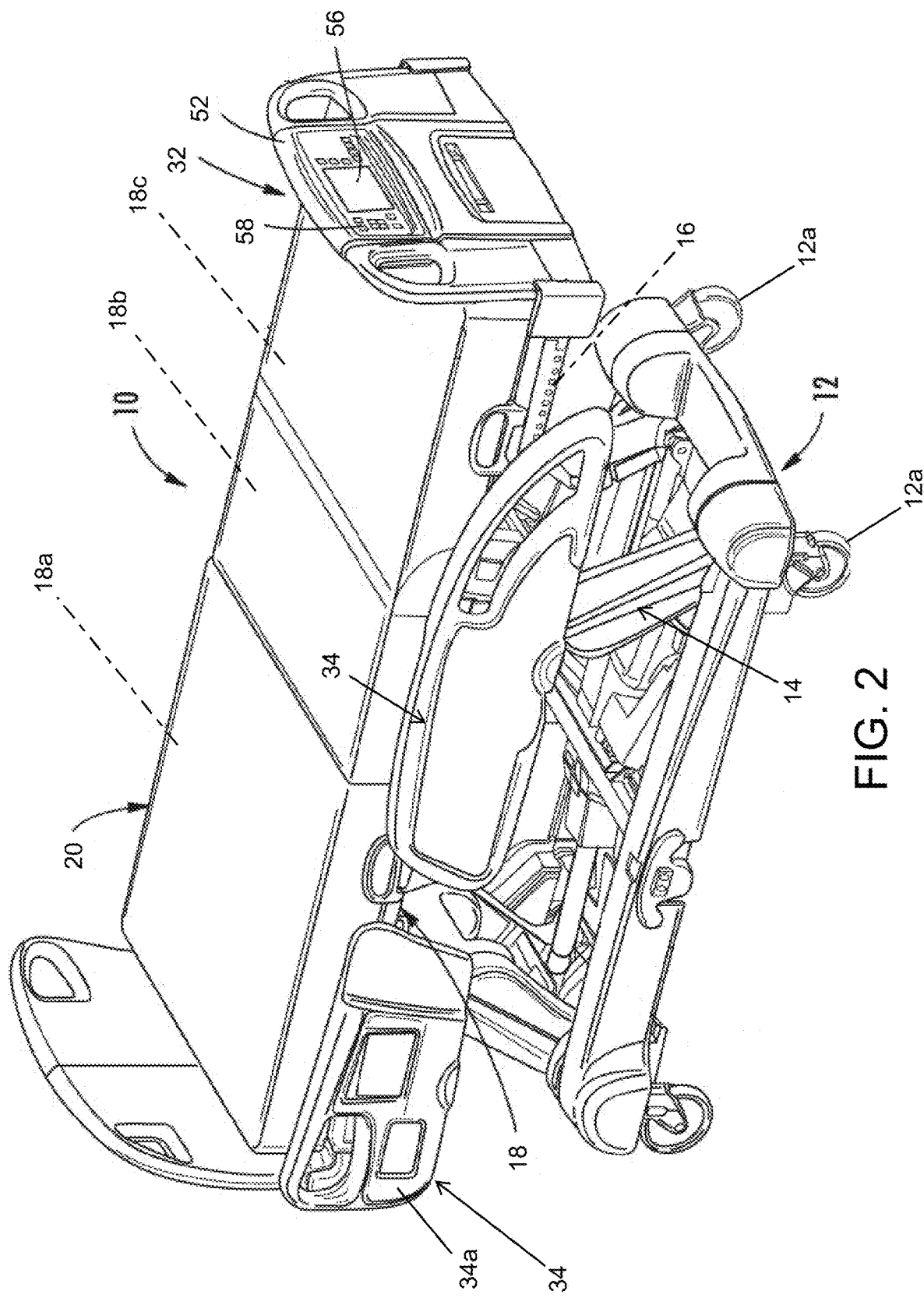
FIG. 2 is a similar view to FIG. 1 illustrating the deck and the mattress of the patient support apparatus in a flat or supine position.
Figure 3:
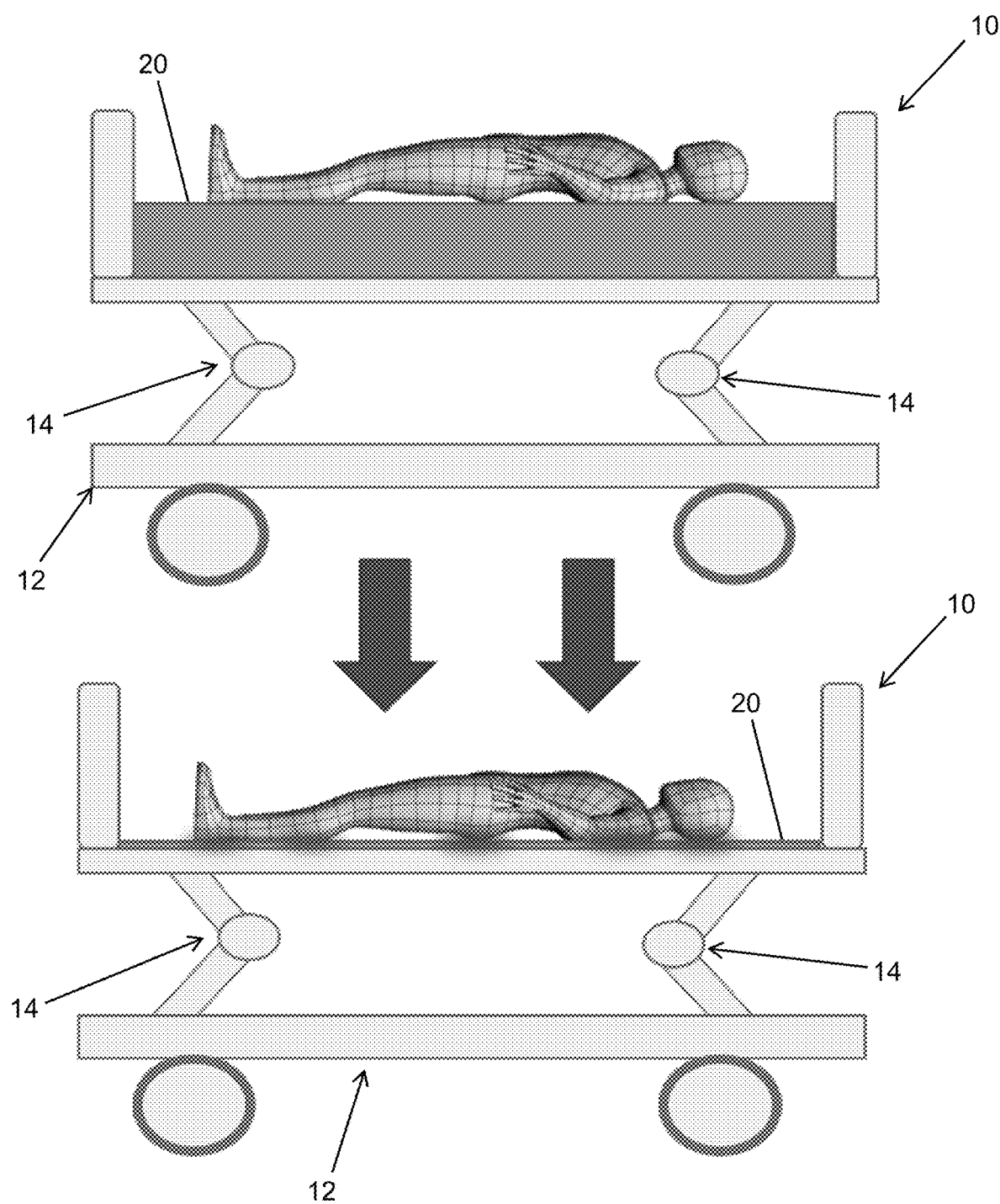
FIG. 3 is side elevation views of the patient support apparatus of FIG. 1 illustrating the mattress in a first state, such as a normal inflated state, and in a second state, such as a fully deflated state for CPR.
Figure 4:
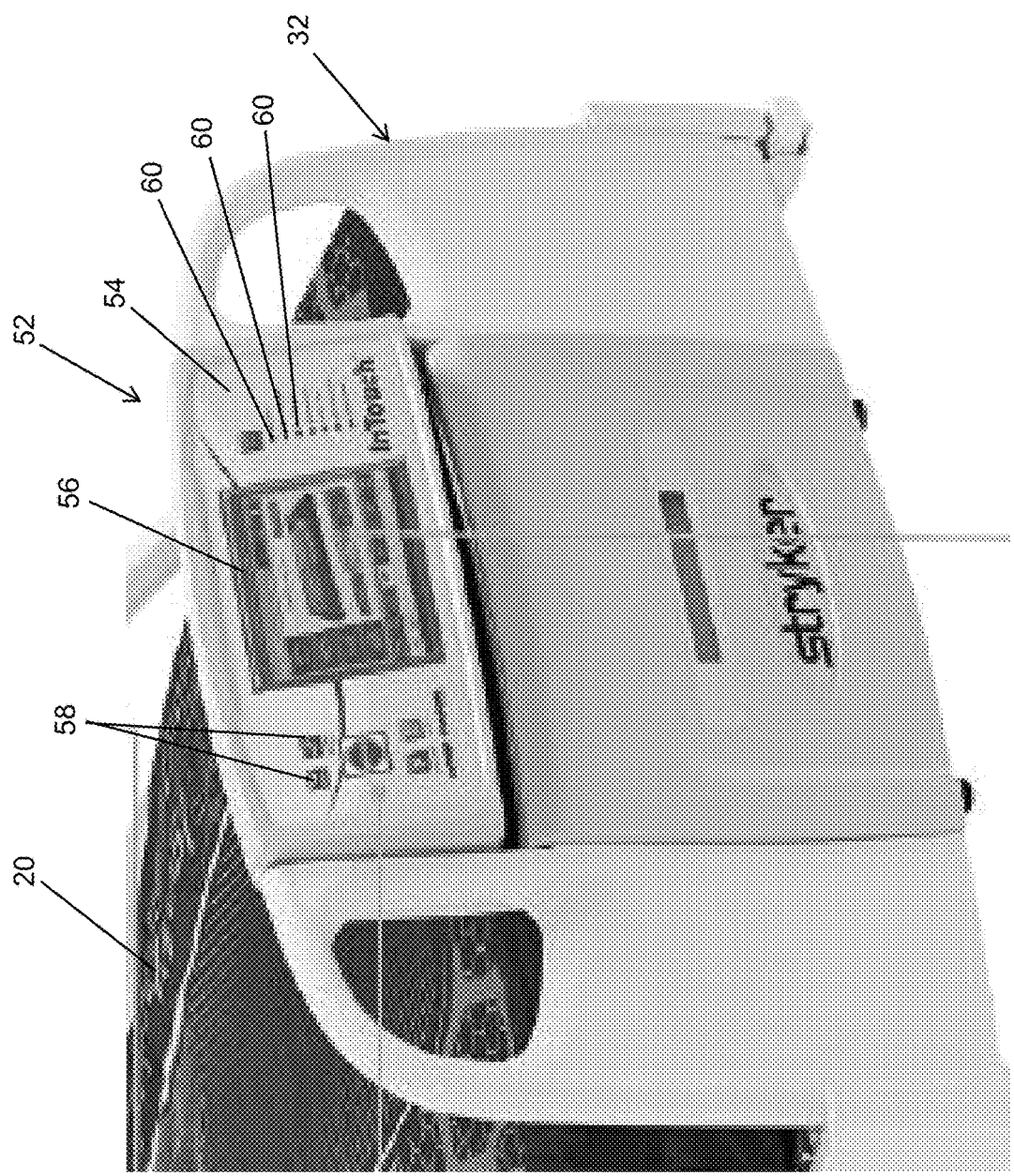
FIG. 4 is an enlarged exploded perspective view of the footboard of the patient support apparatus.

As best seen in FIGS. 1 and 2, patient support apparatus 10 includes a base 12, with a plurality of bearings 12a, such as caster wheels, a lift assembly 14, and a deck frame 16, which is supported by the lift assembly 14 and which supports a deck 18. The deck 18 is an articulatable deck and supports a mattress 20 thereon. As will be more fully described below, mattress 20 may include an inflatable portion or be entirely inflatable with a plurality of bladders 22 that may have a variety of different configurations. For examples of suitable mattresses with bladders, reference is made to U.S. application Ser. No. 12/640,643 (P239B) filed Dec. 17, 2009, U.S. Pat. No. 8,911,387 (P257A) issued on Dec. 16, 2014, and U.S. Pat. No. 9,782,312 (P405F), which are commonly owned by Stryker Corporation of Kalamazoo, Michigan, and are incorporated by reference in their entireties herein.

Patient support apparatus 10 further optionally includes a headboard 30, a footboard 32 (which may be removable), and a plurality of side rails 34. Side rails 34 are all shown in a raised position (in FIG. 1) but are each individually movable to a lower position to allow ingress into, and egress out of, patient support apparatus 10. For examples of side rails, footboards, and headboards, reference is made to U.S. Pat. No. 7,962,981 (P102C) issued on Jun. 21, 2011, and U.S. application Ser. No. 15/218,500 (P474A) filed on Jul. 25, 2016, which are commonly owned by Stryker Corporation of Kalamazoo, Michigan, and are incorporated by reference in their entireties herein.

In addition, patient support apparatus 10 includes a control system 40 with a bed-based or main controller 50. Controller 50 includes any and all electrical circuitry and components necessary to carry out the functions and algorithms described herein, as would be known to one of ordinary skill in the art. Generally speaking, controller 50 may include one or more microcontrollers, microprocessors, and/or other programmable electronics that are programmed to carry out the functions described herein. It will be understood that controller 50 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/ or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions or they may reside in a common location. When physically distributed, the components may communicate using any suitable serial or parallel communication protocol, such as, but not limited to, CAN, LIN, Firewire, I-squared-C, RS-232, RS-485, universal serial bus (USB), etc.

Figure 5:
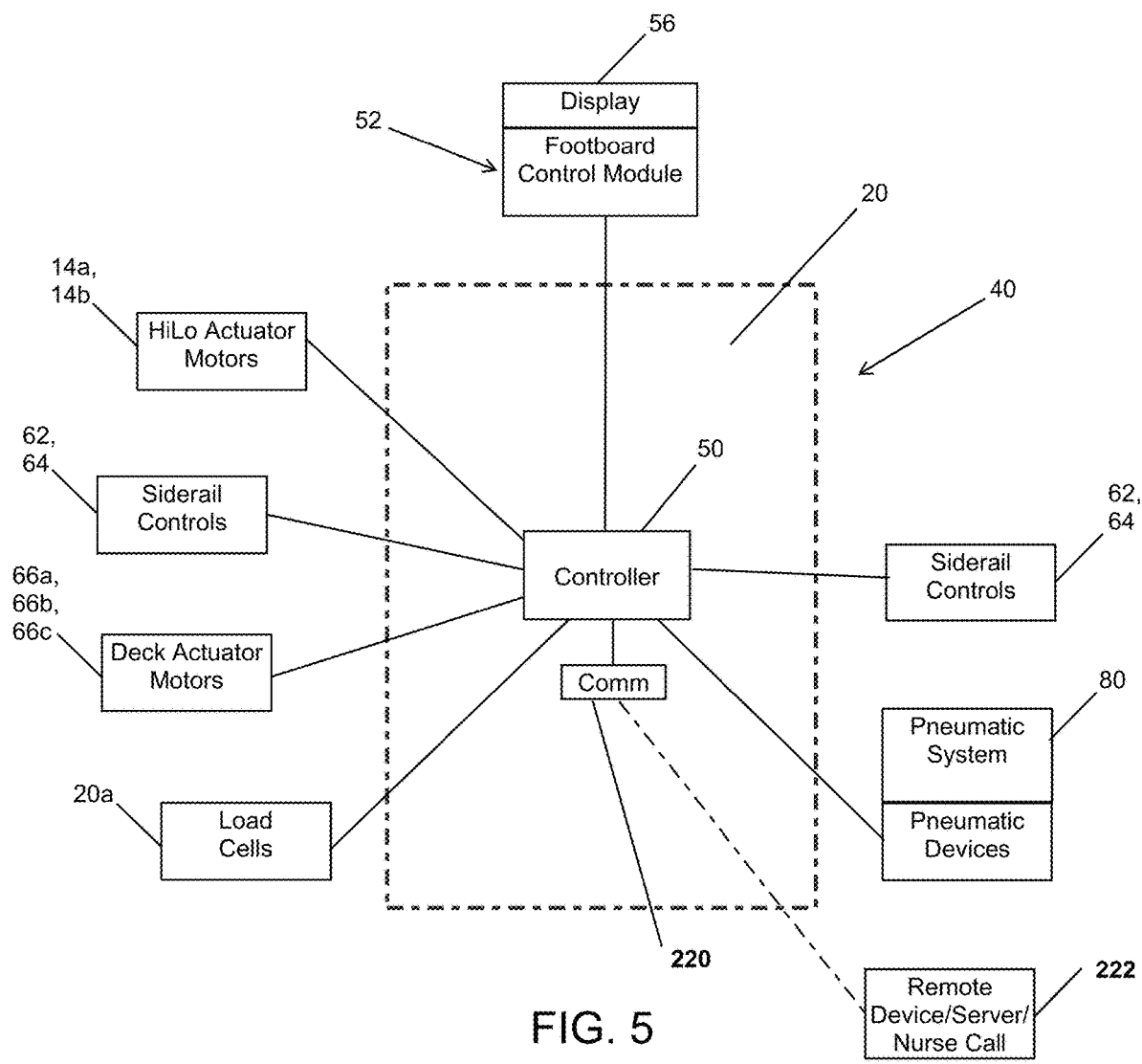
FIG. 5 is a simplified schematic plan view of the layout of the control system in the patient support.

Control system 40 also includes a control module 52, which is optionally mounted in foot board 32 (FIG. 1). Control module 52 includes a control panel 54 (FIG. 1) with a plurality of user interface devices, such as a display 56, for example a touch screen display, buttons 58, and indicators 60, which are in communication with controller 50. Referring to FIG. 5, controller 50 in turn is in communication with the bed actuators, such as the lift actuators, deck actuators, the pneumatic devices that control the inflation or deflation of the mattress, as well as sensors to detect the state of the various components of the bed.

Control panel 54 is configured to allow a caregiver to control movement of the deck 18 and lift assembly 14, and further to control inflation/deflation of mattress 20 and actuate various functional systems at the patient support apparatus, such as a bed exit system, a scale (weighing) system, for example, via controller 50 or other controllers that are included in the control system.

Suitable indicators 60 include lights, such as LED lights, that are powered by control system 40 to provide an indication of a variety of functions, such as when a bed exit system is active, when the bed is plugged in, when the bed is charging, when the brake is not set, when the battery is low, when to call maintenance, or when control locks are enabled. And further, as described below, indicators 60 may provide an indication of when to reset or return the mattress to its pre-treatment state.

For examples of a suitable control modules, control panels, displays, buttons, and indicators and bed function systems noted above, reference is made to U.S. Pat. No. 7,962,981 (P102C) issued on Jun. 21, 2011 and U.S. Pat. No. 9,038,217 (P199) issued on May 26, 2015, which are commonly owned by Stryker Corporation of Kalamazoo, Michigan, and are incorporated by reference in their entireties herein.

Control system 40 may include additional controls, such as caregiver controls 62 and patient controls 64 mounted in one or more of the side rails 34, such as in the head end side rails 34a, which allow the caregiver and/or the patient to control various functions of the bed. Again, for examples of suitable controls reference is made to U.S. Pat. No. 7,962, 981 (P102C) issued on Jun. 21, 2011 and U.S. Pat. No. 9,038,217 (P199) issued on May 26, 2015, which are commonly owned by Stryker Corporation of Kalamazoo, Michigan, and are incorporated by reference in their entireties herein.

Deck 18, as noted, is an articulatable deck with one or more movable deck sections, such as a back section 18a, a seat section 18b, and a leg deck section 18c (FIG. 2). Each articulatable section, such as the back section 18a, the seat section 18b, and the leg section 18c, may have a motorized actuator (back section actuator 66a, seat section actuator 66b, leg section actuator 66c—see FIG. 5) associated therewith to move their respective deck section to adjust the configuration of the deck 18. Suitable deck sections and actuators are described in U.S. Pat. No. 7,962,981 (P102C) issued on Jun. 21, 2011 and U.S. Pat. No. 9,038,217 (P199) issued on May 26, 2015.

Optionally, to quickly move (e.g. lower) at least the back section 18a of deck 18, for example in a situation when a patient needs cardiopulmonary resuscitation (CPR), patient support apparatus 10 may include a CPR drop mechanism that allows the back section 18*a* to lower quickly. The CPR drop mechanism may be a mechanical mechanism or an electro-mechanical mechanism that quickly retracts the back section actuator. For examples of suitable CPR drop mechanisms reference is made to U.S. Pat. No. 7,836,531 (P216A) issued on Nov. 23, 2010, U.S. Pat. No. 9,295,598 (P456A) issued on Mar. 29, 2016, and U.S. patent Ser. No. 10/875, 335 (P453A), filed on Jun. 25, 2004, which are all commonly owned by Stryker Corporation of Kalamazoo, Michigan, and are incorporated by reference in their entireties herein.

As noted above, mattress 20 includes at least an inflatable portion that forms at least a portion of the head end of the mattress. Additionally, as will be more fully described below, the control system 40 includes a pneumatic system 80 with a pump 82 and valving (FIG. 6) to direct the flow of air to the inflatable portion of the mattress. In addition, control system 40 is configured to quickly deflate the inflatable portion of the mattress 20 so at least the back or chest area of the patient can rest on the flat hard surface of the deck 18 and allow a caretaker to administer CPR to the patient.

As noted above, the inflatable portion may be formed from a plurality of bladders 22. For example, bladders 22 may comprise a plurality of discrete bladders (that may or may not be in fluid communication with each other) or a bladder layer with a plurality of air cells or pods that form bladders, some of which may be in fluid communication with each other. For example, the bladders may be formed from transverse bladders that extend across the width of the mattress or pod-like bladders, such as disclosed in U.S. application Ser. No. 12/640,643 (P239B) filed on Dec. 17, 2009, U.S. Pat. No. 8,911,387 (P257A) issued on Dec. 16, 2014, and U.S. Pat. No. 9,782,312 (P405F), which are commonly owned by Stryker Corporation of Kalamazoo, Michigan, and are incorporated by reference in their entireties herein.

Figure 6:
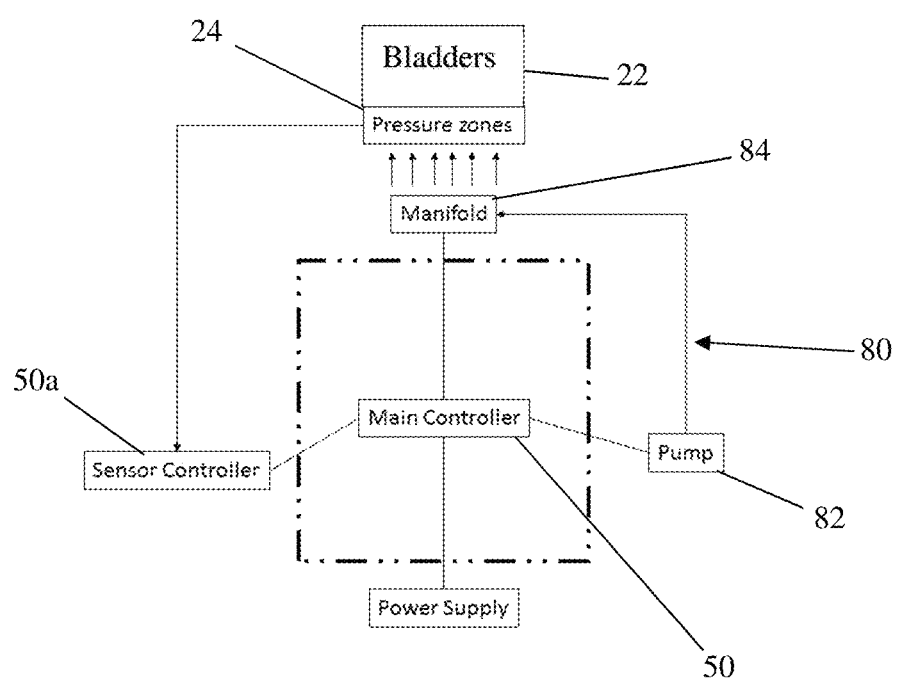
FIG. 6 is a schematic drawing of the pneumatic system of the control system of the patient support.

To control the inflation of the bladders 22, and referring to FIG. 6, patient support apparatus 10 includes pneumatic system 80, as noted. Pneumatic system 80 includes at least one pump 82 (and an associated motor) and various tubing and valves to control the flow of air through pneumatic system 80 to inflate or deflate bladders 22 (and other additional bladders) that are contained in mattress 20. For example, additional bladders may be provided to provide a turning function, which are also controlled by pneumatic system 80, or percussion and/or vibration treatment. Pump 82 (via its associated motor) and the various valves, for example control valves and solenoid valves, are controlled by controller 50.

In one embodiment, pneumatic system 80 includes a CPR valve manifold 84, which is in fluid communication with at least the head end bladders (or all the bladders if only head end bladders are provided) and which directs air flow from pump 82 to the bladders. Manifold 84 may include a plurality of solenoid valves with three positions—open between the air supply (via the pump) and the bladders, closed, or open between the bladders and the atmosphere. Thus, when opened to atmosphere, manifold 84 can discharge the air from all the bladders so that the patient can quickly bottom out on the underlying deck 18. For an example of a suitable CPR valve manifold reference is made to U.S. Pat. No. 8,201,292 (P105B), which issued on Jun. 19, 2012, and is commonly owned by Stryker Corporation of Kalamazoo, Michigan and is incorporated by reference in its entirety herein. For example, the CPR valve manifold 84 may include a manual pull strap, which is accessible at the side of the patient support apparatus 10 adjacent deck 18 and mattress 20, and further may include an automatic reset mechanism to close the valve manifold 84, such as described in the referenced patent.

In another embodiment, air from the bladders may be exhausted through a CPR pressure regulator valve, which is powered and in communication with controller 50 so that, as described below, the pneumatic system 80 can be automatically reset the valve after CPR and configured to automatically inflate the bladder or bladders that were deflated for CPR. Optionally, rather than dumping the air from the bladders, the pump and regulator valve may be configured to suction out the air from the mattress bladders during a CPR event.

In a hospital (or other type of patient care settings), as noted above, patients who are supported on patient support apparatus 10 may experience an episode in which cardio-pulmonary resuscitation (CPR) needs to be performed on the patient. CPR is typically performed on a patient who is supine (lying flat on their back) on a generally horizontal, rigid surface. Though it may be beneficial in some circumstances to have the back section ("Fowler") raised above horizontal at an angle, for example, in some cases the Fowler may be raised to an angle, such as a 30 degree angle, a 60 degree angle, or an angle between 30 degrees to 60 degrees. Other angles may also be possible. In any of these situations, it is desirable to have the deck 18 move to its desired CPR configuration (e.g. supine orientation (flat configuration) or angled configuration) and either deflate the mattress 20 so that the patient is essentially bottomed out on the deck 18 or to inflate the mattress 20 to a high pressure (or "max inflate") where the mattress is sufficiently rigid to perform CPR compressions on the patient.

As noted above, patient support apparatus 10 may include a CPR release mechanism, which quickly lowers at least the back section of deck 18 to its desired CPR configuration. Further, as noted the CPR release mechanism may be mechanical or an electro-mechanical mechanism. In an electro-mechanical application, control system 40 may be configured with a user input device, which when actuated sends a CPR actuate signal to the controller 50. In response to the CPR actuate signal, controller 50 may be configured to drive at least the back section deck actuator, and optionally all the deck actuators, so that at least the back section and optionally all the deck sections are moved into their CPR configuration, such as a flat supine configuration. Suitable user input devices include a button or a portion of the touch screen at control module 52, or at other caregiver controls, including remote controls. Remote controls may include hand held controls, including phones, electronic pads, or other hand held devices, or a nurse call station computer, which may be configured to control the patient support apparatus using wired or wireless communication with control system 40.

For example, the CPR configuration may include positioning of the leg section 18*c*, the seat section 18*b*, and the back section 18*a* of deck 18 so that they are aligned and in a generally horizontal position. Although it will be understood that in some embodiments, the CPR configuration does not include positioning of leg section 18*c* into the horizontal position. It should be understood that patient support apparatus 10 may also be placed into the CPR configuration at times other than when CPR is being performed.

Controller 50 may be further programmed to coordinate the movement of back section, seat section, and leg section actuators 66*a*, 66*b*, and 66*c* such that movement of back section 18*a* occurs concurrently with the movement of seat section 18b and/or leg section 18c. For example, after the CPR function is selected, for example at control module 52, controller 50 may be configured to control back section actuator 66a to move back section 18a to the horizontal position (or angled position as noted above). As described in the referenced patent, a separate manual actuator may also be present that assists in the movement of back section 18a to the horizontal position (or angled position). Simultaneous (or sequential) movement of seat section 18b and/or leg section 18c may also occur so that the deck is reconfigured into a flat and optionally horizontal configuration.

After the emergency situation (e.g. CPR event) is over, controller 50 may control the various actuators to move them to their pre-CPR event state or to a predetermined configuration. As will be more fully described below, controller 50 may further inflate bladders 22 of mattress 20 to their pre-treatment inflation state, e.g. pre-CPR event state, or to a predetermined inflation state, or simply notify the caregiver to do so.

As noted above, in one embodiment, control system 40 is configured to generate a notification to remind to a caregiver to change the state of the inflatable mattress portion, for example, after a treatment event, such as a CPR treatment. Optionally, control system 40 is configured to generate a notification that is indicative of a selected state of the inflatable mattress portion, for example a CPR state, to provide a reminder to a caregiver to change the selected state of the inflatable mattress portion.

For example, the selected state may comprise a reduced pressure state, such as a deflated state during a CPR event, with control system 40 generating the notification when the inflatable mattress portion is in the deflated state.

Figure 7:
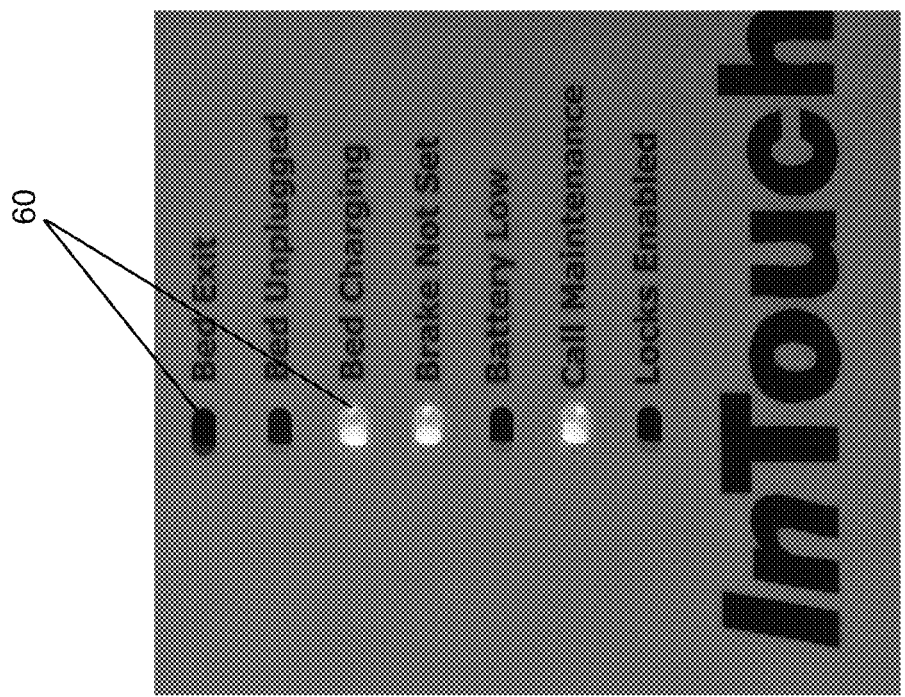
FIG. 7 is an enlarged view of a portion of a control panel mounted to the footboard of the patient support apparatus.

In one embodiment, such as shown in FIG. 7 and as noted above, the patient support apparatus includes indicators 60 in the form of light assemblies, such as LED lights. The notification may be in the form of the control system powering one of the light assemblies 60 to generate the notification. In addition, the patient support apparatus 10 may include indicia in the form or words or a symbol associated with the light assembly (60) to indicate the treatment associated with the selected state of the mattress, e.g. the indicia may be the letters "CPR" or "call maintenance" or a mattress icon or another icon, described below. In one embodiment, the control system 40 is configured to flash the indicia to assist in drawing attention to the indicia.

In addition, control system 40 may be configured to cause the light assembly to flash or generate a different color or light intensity (for example in the case of a tunable LED) or the light assembly used for the notification can be configured itself to generate a different color or intensity than the other light assemblies. The light indicator notification, including the flashing light indicator notification, may be implemented alone or in addition to any of the other notifications described herein.

In one embodiment, the control system 40 generates a sound, such as a chirp, as the notification or in addition to the other notifications described above. For example, control system 40 may include a noise generator device (e.g. a buzzer) or a speaker that outputs a sound generated by controller 50 (e.g. using a noise generator application software) or outputs a recording stored in the control system's memory. In one embodiment, after a set period of time after the activation of CPR, the sound, such as the audible chirp, will go off periodically until CPR is deactivated (e.g. when the CPR valve is closed and mattress is re-inflated). Similarly, the sound indicator notification may be implemented alone or in addition to any of the other notifications described herein.

In another embodiment, as noted, the notification can be in the form of an icon 90, for example at display 56. Icon 90 can immediately notify the caregiver that CPR is activated. For example, as noted below, icon 90 may only appear when the CPR is active or maybe always resident but may change its appearance when the CPR is active. In other words, the icon can change from a first state when CPR is inactive and change a second state when CPR is active.

Figure 8:
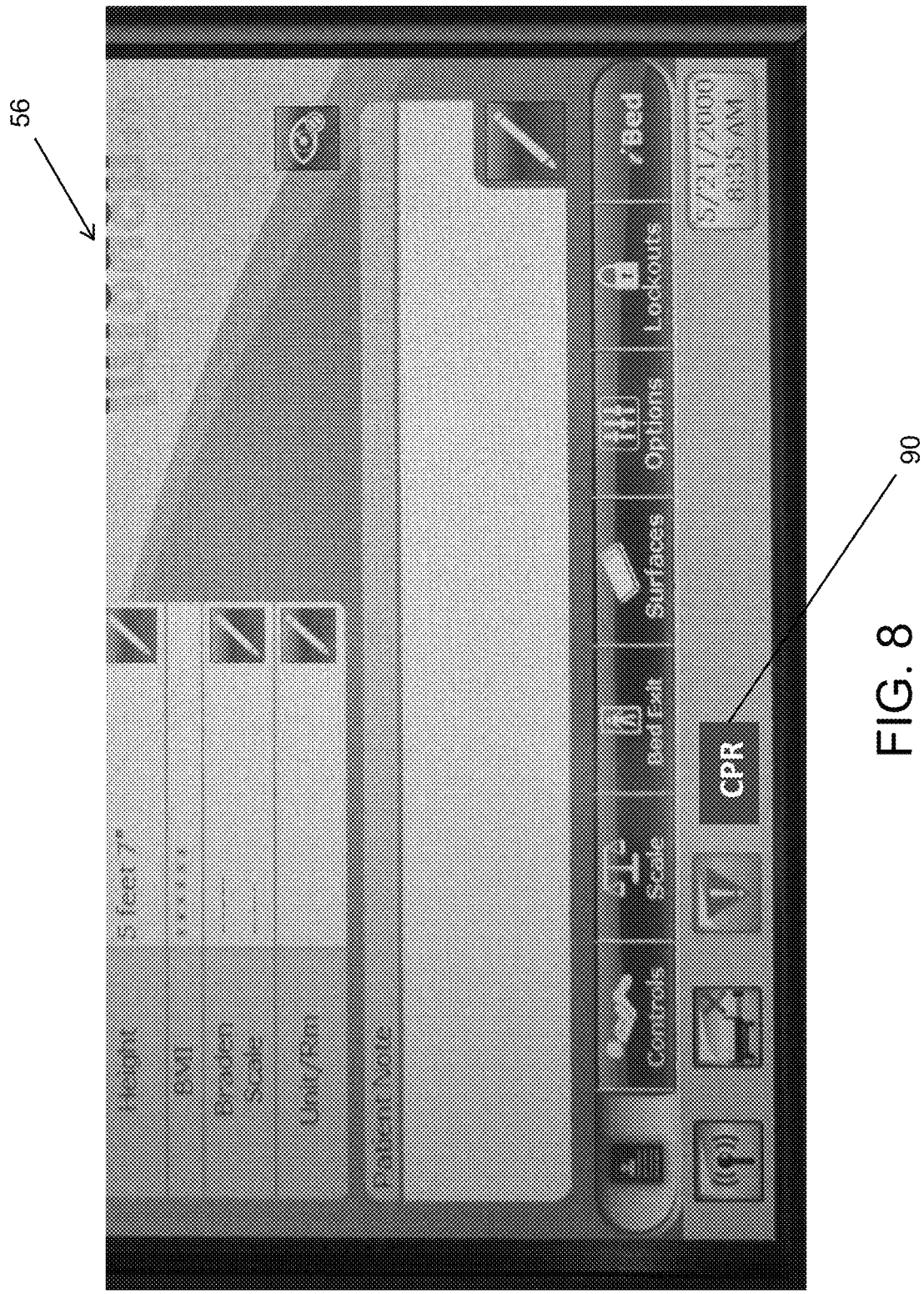
FIG. 8 is an enlarged view of a display of the control panel mounted to the footboard of the patient support apparatus.

As best seen in FIG. 8, in one form, icon 90 is generated as a text box at display 56, for example, at the lower edge of display 56 adjacent other indicators beneath the control buttons formed in the display. Icon 90 may include a symbol or word or image to convey to a caregiver the selected state of the mattress, e.g. CPR for a CPR state. Control system 40 may generate a static icon or a dynamic icon, for example, an icon that changes—flashes, changes color, or any other change that would help flag the icon to a caregiver. In one embodiment, the icon is always generated but then changes to provide the notification. For example, the icon may be greyed out when the mattress is not in the selected state and then no-longer greyed out when the mattress is in the selected state.

Optionally, icon 90 may be configured as a control button so that when it is selected by pressing, control system 40 will redirect a user to the page associated with the mattress control menu (referred to as "surface menu") where the user can control the inflation or deflation of the mattress, as well as other mattress functions.

In another embodiment, the notification generated by control system 40 may be in the form of a mattress icon, such as an overlay that is generated over whatever window is currently displayed on display 56, or as a control button (as noted above) (along with other control buttons, for example that are located at the bottom on the screen as shown in FIG. 8) that allows a user to be redirected to the mattress control menu ("surface menu").

In one embodiment, the notification may be in the form of existing mattress icon, which is then modified to add additional indicia.

Figure 9:
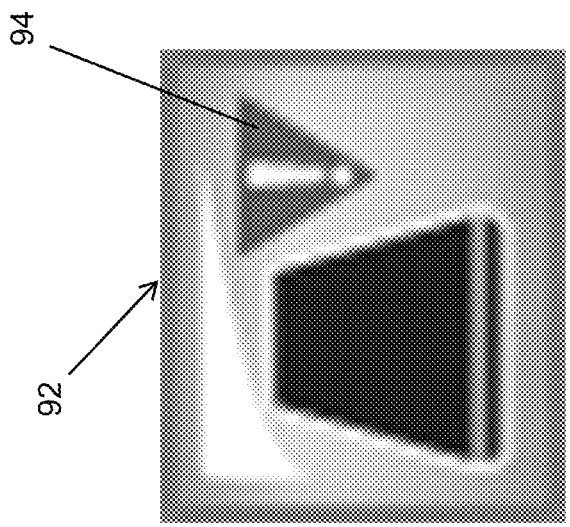
FIG. 9 is an enlarged view of an icon that can be generated on the display of FIG. 8.

For example, referring to FIG. 9, the mattress icon 92 (whether an overlay window or an existing control button) may include an image of the mattress, such as shown, and an alert symbol 94, such as shown in the form of an inverted triangle with an explanation point, which alerts the caregiver that there is something urgent about the mattress. The alert symbol may be the letters CPR so that it is self-evident to what the urgency relates.

It should be understood that any of the icons mentioned (e.g. CPR or mattress) can be just an icon at the bottom of the screen along with the other control buttons and icons. Alternately, as noted, the icon may be an overlay over another portion of the window.

Figure 10:
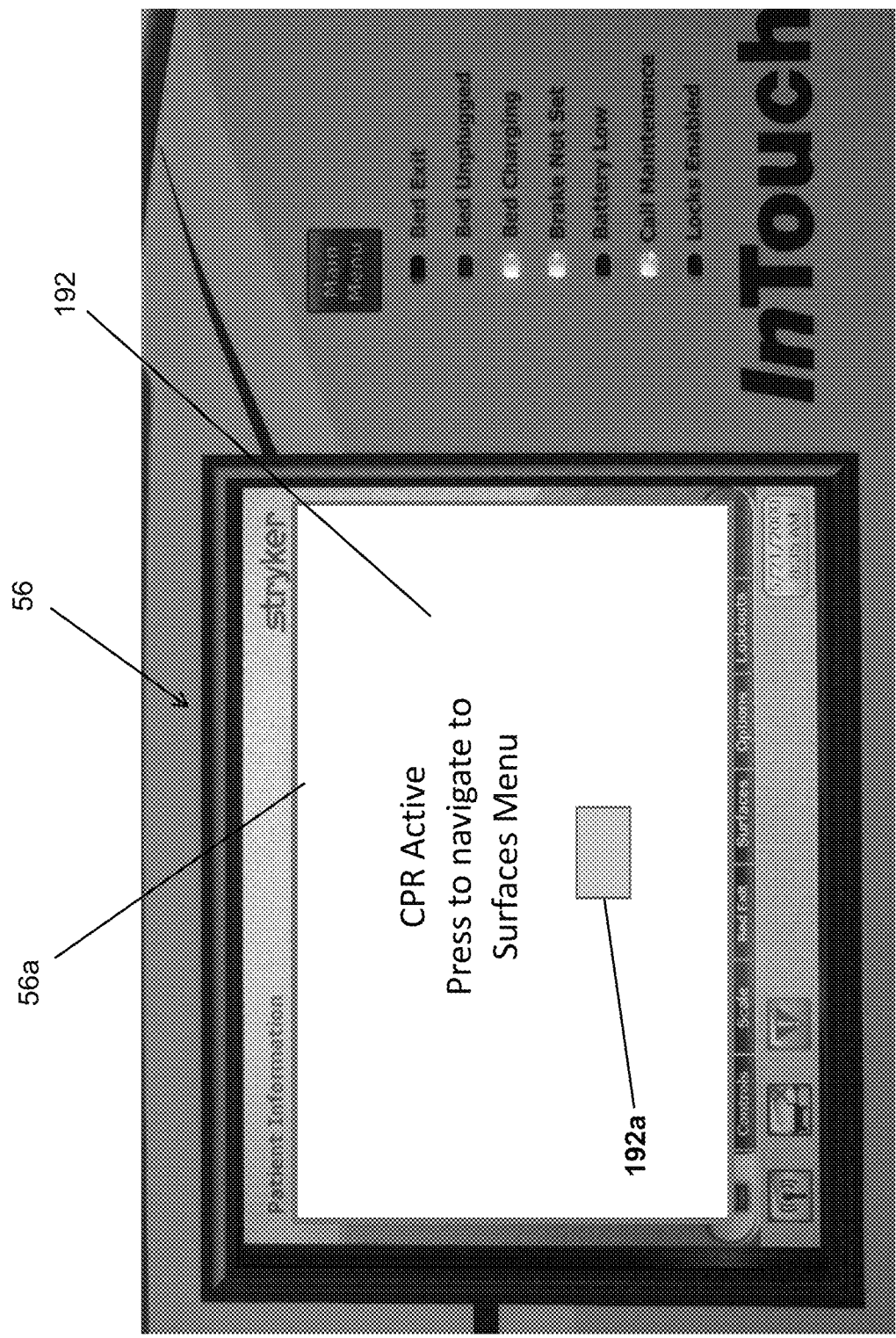
FIG. 10 is an enlarged view of the control panel and the display with a notification window overlay.
Figure 11:
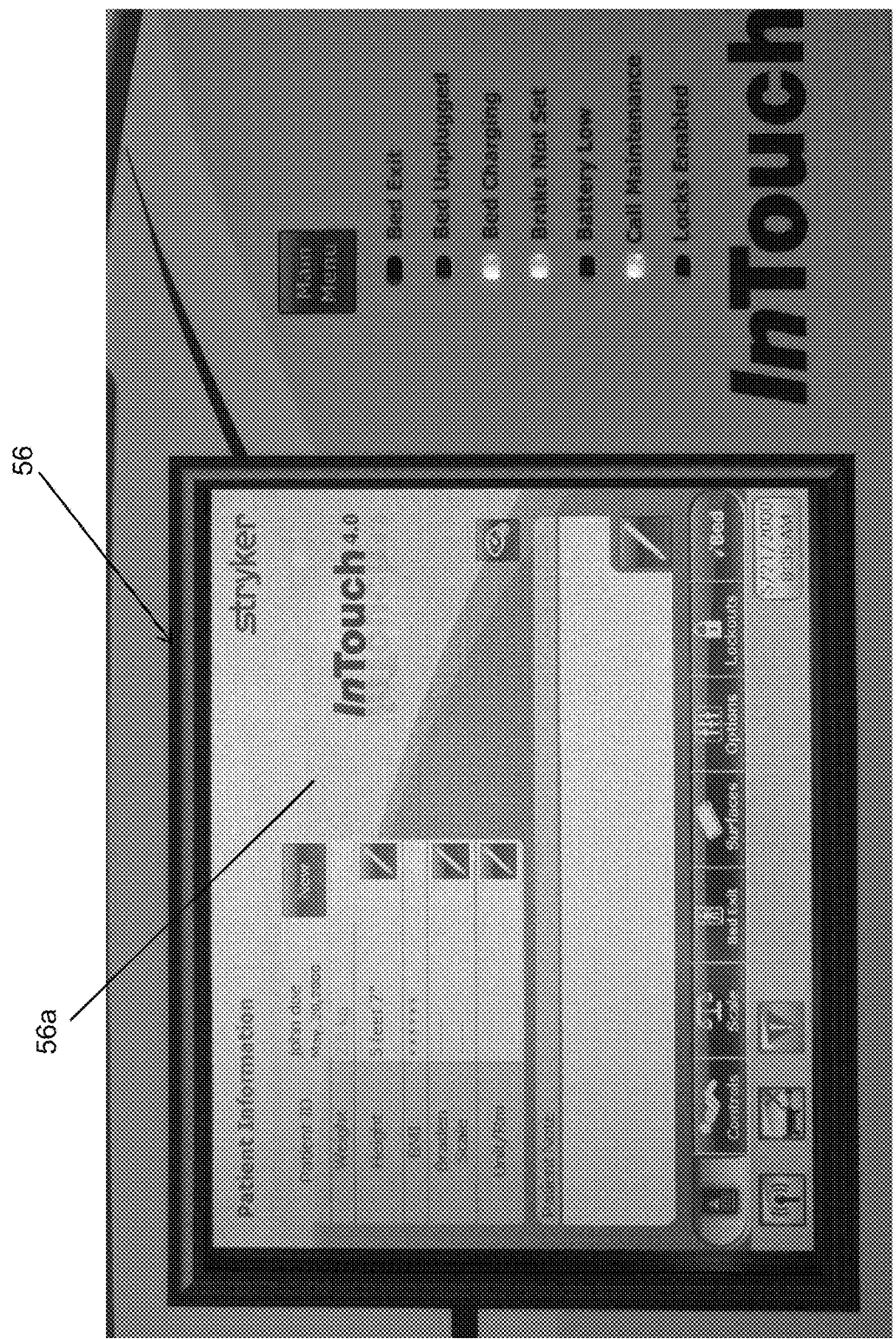
FIG. 11 is a similar view to FIG. 10 with the notification window overlay removed.

In another embodiment, referring to FIGS. 10 and 11, the notification may be in the form of a notification display window 192. For example, the display 56 may generate a home screen or other functional control template screen 56a, with the notification display window 192 covering at least a portion of or a majority of the home screen for at least a preselected period of time. Optionally, the notification display window 192 may cover most of the underlying screen and block access to one or more of the icons or control buttons of the screen that it overlays. Alternately or in addition, control system 40 may lockout one or more of the controls, for example only leaving the mattress controls available to allow the caregiver to re-inflate the mattress. In one embodiment, control system 40 may lockout one or more of the controls at the control module 52 only, leaving the controls active and available for use at the other controls (66,68).

Notification display window 192, as shown, may be simply a window with a notice that the CPR is active and instructions for the caregiver to navigate to the mattress or "surface" template or window. Optionally, window 192 may include a button 192a that may be used by a caregiver to indicate they acknowledge that the CPR is still active (and the mattress is bottomed out).

After the preselected period of time has passed, control system 40 may no longer display notification display window 192 so that the user may still have access to the controls or information on display 56a, such as shown in FIG. 11. After a second selected period of time, control system 40 may redisplay notification display window 192 over the home screen (or whatever screen the user has switched to) again for the first preselected period of time. This display and removal of the display may be repeated (by control system 40) until the user has reset the mattress back to its pre-treatment state or to a preselected state or has otherwise been indicated that the CPR is deactivated (in other words, the bed is now in its pre-CPR state or in another non-CPR state). For example, control system 40 may detect the state of the mattress (CPR state or non-CPR state) by using pressure sensors in the inflatable portion of the mattress or based detecting the input that triggers the re-inflation of the inflatable portion of the mattress.

In one embodiment, as generally noted above, control system 40 may be configured to lockout one or more of its controls at the user input devices, such as control module 62 and/or controls 62 and/or 64. In this manner, a caregiver would be forced to "deactivate" on the CPR In one embodiment, mattress 20 may be configured to communication with controller 50 (or a remote device), including wirelessly, to indicate when the mattress has been configured in a treatment and/or when it is reset after a treatment event. For a suitable mattress wireless communication system, reference is made to U.S. Pat. No. 9,289,336 (P382A), which is commonly owned by Stryker Corporation of Kalamazoo, Michigan, and is incorporated by reference in its entirety herein.

In another embodiment, the control system 40 is configured to automatically modify the selected state of the inflatable mattress portion in response to (1) a passage of time after the selected state was input into the control system or (2) one more triggers, such as a sensed condition at the mattress.

Figure 12A:
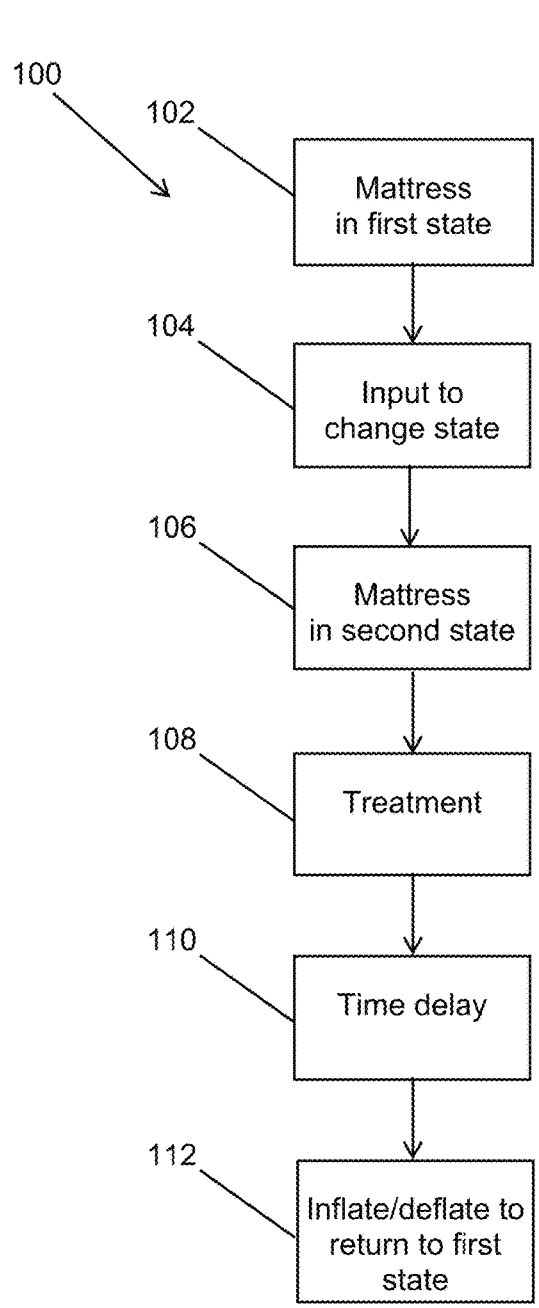
FIG. 12A is a flow chart of an event at the patient support apparatus and the automated process for returning the mattress of the patient support apparatus to its pre-event state.

Referring to FIGS. 12 and 12A, control system 40 is configured to automatically modify the selected state of the inflatable mattress portion in response to a passage of time. For example, control system 40 is configured, for example via software, to perform an automated re-inflation (or deflation) process (100). Automated re-inflation (or deflation) process 100 may start when the mattress 20 of patient support apparatus 10 changes or is changed from a first state (102), based on input (to change its state) (104), to a second or treatment state (106). After treatment is applied or has occurred (108), control system 40 is then configured to generate a time delay (110), and thereafter (after the time delay) re-inflate (or deflate) the inflatable mattress portion to its first state (or to a preselected state) (112).

In another embodiment, control system 40 measures the time (e.g. using a timer in controller 50) once the inflatable mattress portion is changed to its second state, and then compares the time to a stored time to determine when to re-inflate (or deflate) the inflatable mattress portion.

Figure 12B:
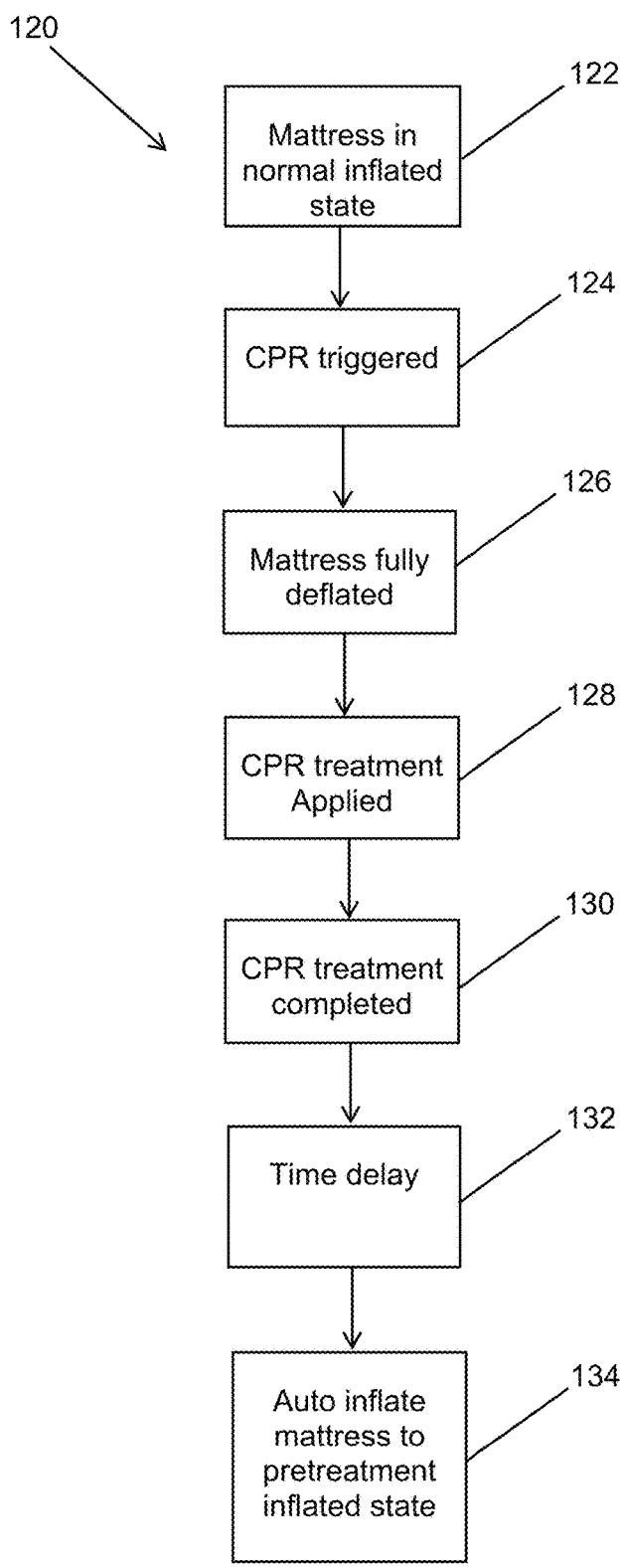
FIG. 12B is a flow chart of a CPR event at the patient support apparatus and the automated process for returning the mattress of the patient support apparatus to its pre-CPR event state.

For example, referring to FIG. 12B, control system 40 may be configured, for example via software, to perform an automated CPR reset process (120). As will be more fully described below, the control system 40 may be configured to detect when CPR is active and then to detect a characteristic associated with CPR and use that characteristic to determine when the CPR is no longer be administered and then inactivate the CPR by re-inflating (or deflating) the inflatable mattress portion (with or without a time delay).

Automated CPR reset process 120 may start when control system 40 detects the CPR process at the patient support is active. For example, control system 40 may be configured to detect that the mattress 20 of patient support apparatus 10 has changed from a normal inflation state (122) to a fully deflated state (or max inflate as noted above). This can be detected by sensing that the mattress has been deflated via sensors (e.g. in the mattress) and/or by sensing the CPR valve has been opened. Alternately or in addition, control system 40 may be configured to detect that CPR is active by sensing when the CPR pedal has been moved to its CPR position, or when the CPR button has been selected by a user to start the CPR process, such as a button at one of the controls (64, 66) or control module 52. Therefore, control system 40 may detect mechanical actuation or electrical actuation of the CPR process, or both.

After the mattress is fully deflated (or at least the head end or back section of the mattress has been fully deflated, such as shown in FIG. 12), and CPR treatment is applied or has occurred (128) and completed (130), control system 40 is then configured to optionally generate a time delay (132) and thereafter re-inflate (or deflate) the inflatable mattress portion to its pre-treatment state or to a selected state (134). As noted, the time delay may be after the CPR process has been completed, or alternately may be triggered after the initiation of CPR, or at some other relevant point in time.

In order to re-inflate the mattress 20, the CPR valve manifold must be closed. As noted above, patient support 10 may include a CPR valve manifold that automatically closes after CPR has been complete. Alternately, the CPR valve manifold may be manually closed. Manual closing of the CPR valve manifold may also be required for an automatic CPR valve manifold, for example, if the automatic CPR valve manifold fails to close to reset itself automatically, for example, due to an obstruction.

To detect when treatment is completed, for example, control system 40 may include one or more sensors 20a (FIG. 5), such as load cells. Sensors 20a may be configured to detect, for example, a force associated with CPR. In one embodiment, the control system 40 automatically modifies the selected state (e.g. CPR state) of the mattress when the control system 40 detects the force associated with CPR is no longer present. For example, when CPR is applied on the patient, a caregiver generates a compression force on the chest of the patient. Those compression forces may be detected (including their waveform—frequency and amplitude) and when ceased can be used to determine when the CPR has ceased or been completed. For example, using the data from the sensors, control system 40 may be configured to receive the data from the sensors and analyze the sensor data for a pattern suggesting CPR is taking place, which could be represented by a pattern of repeated spikes in the detected force over relatively short periods of time. After the pattern has stopped or ceased, the control system 40 may be configured to re-inflate the mattress.

Optionally, as noted above, the control system 40 may be configured to re-inflate the mattress after a period of time after the pattern has ceased. As such, the control system 40 may automatically modify the selected state of the mattress when the control system 40 detects the force or forces associated with CPR are no longer present after a period of time.

In another embodiment, the control system 40 uses the sensors 20*a* to determine when there has been an increased weight at the mattress 20 while the CPR is active and then when that increased weight has been removed uses the removed weight to indicate when CPR has been stopped. For example, the control system 40 may be configured to automatically modify the selected state (e.g. CPR state) when the increased weight is removed. For example, the weight may be associated with the weight of an emergency medical technician (EMT), or other caregiver, or the weight of a CPR device, such as a Lucas chest compression device, available from Stryker Corporation. When applying CPR to a patient, an EMT or caregiver may climb onto the patient support apparatus, thus adding significant weight to the mattress and supporting deck. The weight may be detected by monitoring the sensors, for example load cells mounted between the deck and deck support frame, and evaluating the pressure distribution on the sensors. Control system 40 may evaluate the signals from the sensors for significant variations in the load sensor signals to determine when the additional weight is initially present and then when the additional weight is removed. For example, the weight of the patient may be used as a baseline, with the control system 40 detecting when there is a significant increase in weight over the baseline weight of the patient, such as a step increase over the baseline weight of the patient.

In other situations, where an EMT does not climb onto the patient support apparatus, then control system 40 may use the force and waveform associated with the application of CPR on a patient, as described above.

Figure 12C:
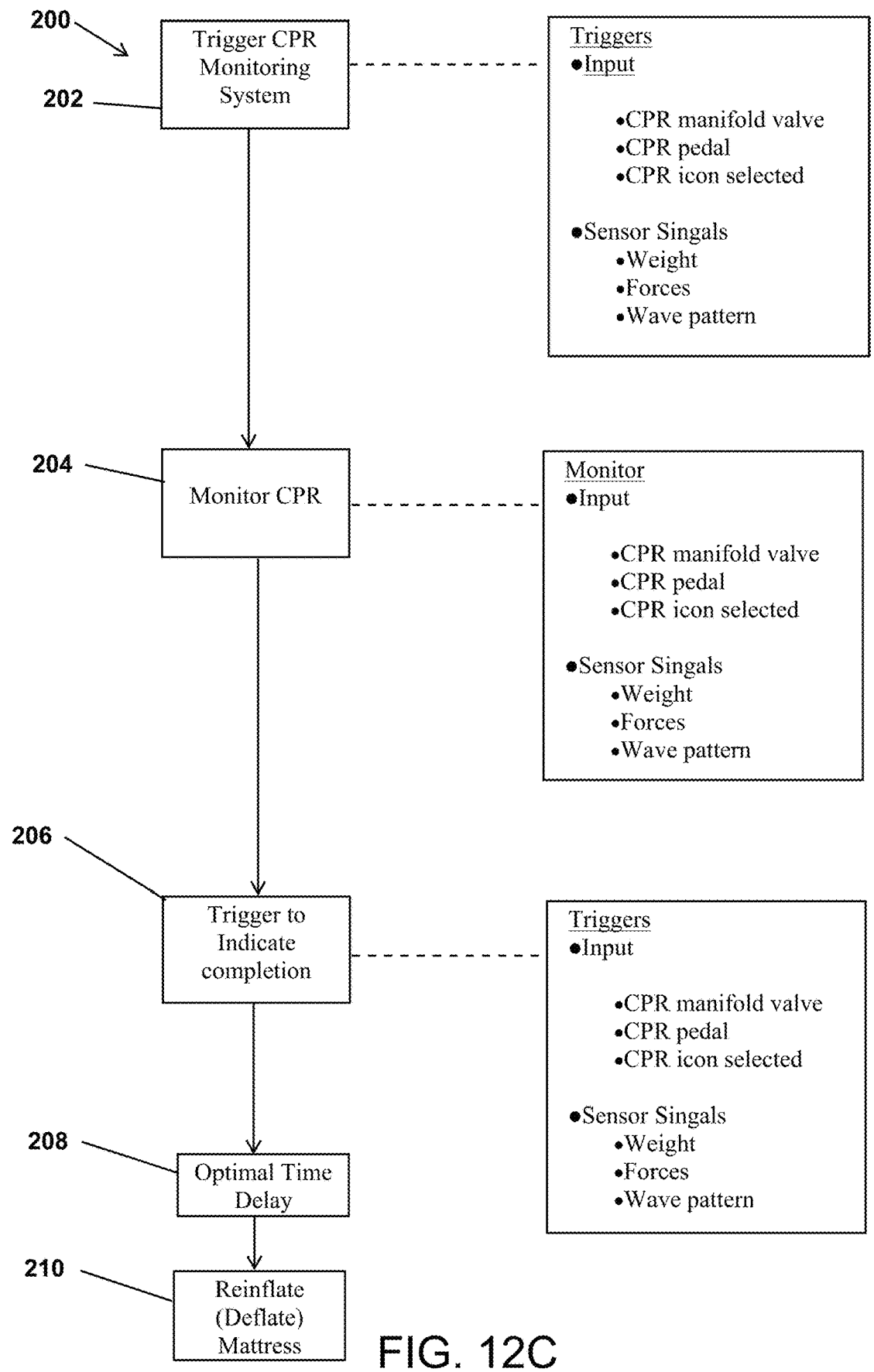
FIG. 12C is a flow chart of another automated process for returning the mattress of the patient support apparatus to its pre-CPR event state.

In one embodiment, referring to FIG. 12*c*, control system 40 may be configured, for example via software, to perform an automated CPR reset process (200). Automated CPR reset process 200 starts with control system 40 monitoring the CPR process. For example, the monitoring process 202 may be initiated by one or more triggers. For example, a trigger may include an input that is a direct indication that the CPR is active, such as detecting via a sensor (which is in communication with the controller 50 or sensor controller 50*a*) when the CPR valve manifold has been opened, for example, electrically by control system 40 or manually by a pull strap or CPR pedal.

Another trigger may include detecting when a CPR pedal has been moved to its CPR position, for example, by a sensor at the CPR pedal, which is in communication with the controller 50 or sensor controller 50*a*.

In yet another embodiment, the trigger may include a CPR icon at a user interface, such as at control module 52, which when actuated by a caregiver generates a signal to control system 40 to initiate the CPR process of deflating (or inflating) the mattress, as described above.

In another embodiment, the trigger may include control system 40 sensing the application of the CPR process, including by sensing the increased weight associated with an EMT or caregiver who is applying the CPR, as noted above. Similarly, the trigger may include sensing the forces and/or wave pattern associate with CPR, as described above.

Once at least one trigger has been detected, control system 40 monitors the CPR process (204). For example, control system 40 may monitor any of the inputs described above that can act as triggers to initiate the monitoring process. Once control system 40 determines that the CPR process is complete (206), control system 40 re-inflates mattress (210), and optionally after a time delay (208).

Control system 40 may be configured to use any one or more of the same triggers noted above to indicate when the CPR process is complete. For example, control system 40 may use input from the CPR valve manifold 84 (e.g. via a sensor) that indicates that the valve is now closed and reset. In another embodiment, control system 40 may sense when the CPR pedal is moved to its non-CPR position as input to indicate that the CPR process is complete. In yet another embodiment, the control system 40 may use a signal from a CPR icon (e.g. located at control module 52) to indicate that the CPR process is complete. Alternately, control system 40 may sense that the weight associated with a caregiver administering CPR is no longer present or the CPR forces are no longer being applied, and/or the CPR wave pattern has ceased to determine that the CPR process is complete. As noted, the time delay may be after the CPR process has been ceased or completed, or alternately may be triggered after the initiation of CPR, or at some other relevant point in time.

As noted above, at least one trigger may be used to initiate control system 40 to monitor the CPR process. Optionally, when the trigger is not a direct indication that CPR is active (e.g. when sensing the weight increase, the force wave pattern) it may be beneficial to use a second trigger, such as a trigger that is a direct indication that CPR is active (e.g. sensing when the mattress is deflated or the CPR valve is open or the CPR pedal is in its CPR configuration or the CPR button has be activated by a use), so that the determination that CPR is active is more accurate.

In any of the above, the control system 40 may be configured to also monitor or sense a condition, such as a biometric, of the patient supported thereon using sensors 20*a* or additional sensors, and then to automatically modify the selected state of the mattress when sensing that the condition of the patient has changed in lieu of or in addition to sensing the force or weight on the mattress (associated with CPR) as detected by the sensors.

For example, in one embodiment, the condition sensed by one or more sensors of the control system 40 comprises a heart rate of the patient.

In another embodiment, the condition comprises a breathing rate of the patient.

For examples of sensors and a control system that can detect conditions or biometrics, such as vital signs, of a patient using sensors, such as load cells, reference is made to U.S. Pat. No. 7,699,784 (P204A), U.S. Pat. No. 9,320,444 (P413C), U.S. patent application Ser. No. 14/873,734 (P442A), and U.S. Pat. No. 9,814,410 (P430A), which are commonly owned by Stryker Corporation of Kalamazoo, Michigan, and incorporated by reference in their entireties herein.

In addition, the control system 40 may be configured to generate a notification to a device remote from the patient support apparatus, with the notification being indicative of the selected state of the inflatable mattress portion to provide a reminder to a caregiver to change the selected state of the inflatable mattress portion.

Referring again to FIG. 5, control system 40 may include a communication device 220, such as wireless communication device, in communication with controller 50 to communicate (one way or two way) with a remote device 222, such as a server (e.g. a hospital server), a nurse call system, or a hand held device, such as a phone or electronic pad or other hand held electronic device. For examples of communication systems that may communicate with remote devices, including a nurse call system, references is made to U.S. Application Ser. No. 62/600,000 filed Dec. 18, 2017 (P575), U.S. Application Ser. No. 62/587,867 filed Nov. 17, 2017 (P576), and U.S. Application Ser. No. 62/598,787 filed Dec. 14, 2017 (P577), which are commonly owned by Stryker Corporation of Kalamazoo, Michigan, and incorporated by reference in their entireties herein.

Further, control system 40 may be configured to send the notification regarding the state of the mattress to a remote device in addition to or instead of the local notifications described above. For examples of suitable communication systems that may be used, including near and far field communication, mesh networks, reference is made to U.S. application Ser. No. 15/959,873 filed Apr. 23, 2018 (P397B), U.S. Application Ser. No. 62/730,217 filed Sep. 12, 2018 (P581), which are commonly owned by Stryker Corporation of Kalamazoo, Michigan, and incorporated by reference in their entireties herein.

As noted above, other treatments that may benefit from the above notification system include an immersion treatment. To that end, control system 40 may also include one or more sensors for each bladder or bladder pressure zone 24 (FIG. 6), which sense the immersion of a patient into the bladders 22 and generate a signal or signals to the main controller 50 or to a sensor controller 50a, which is in communication with controller 50. Based on the signals from the immersion sensor(s), the main controller 50 will adjust the pressure in the respective bladders 22 so that the immersion is adjusted to a pre-determined magnitude or to a selected magnitude, but will generate a notification to the caregiver that an immersion treatment is in effect and to remind the caregiver to return the mattress to a pre-treatment immersion or preselected immersion level after a period of time. In some situations, for example, when a patient is unconscious, a full immersion may be suitable but when a patient is awake and wanting to move, a full immersion state may not be desired. Hence, control system 40 may be configured to either notify a caregiver after a period of time or in response to detecting that a patient is no longer unconscious. For examples of suitable patient monitoring systems, which can detect when a patient is alert and/or moving, reference is made to U.S. Pat. No. 9,320,444 (P413C), U.S. patent application Ser. No. 14/873,734 (P442A), and U.S. Pat. No. 9,814,410 (P430A).

Alternately, similar to the process described above, control system 40 may automatically adjust the immersion or return the mattress to the pre-treatment state based on the above noted input.

For further details of the other bed base functions that may be controlled by control system 40 (other than the mattress functions described above), reference is made to the above referenced patents and copending applications.

While several forms of the patient support have been shown and described, other changes and modifications will be appreciated by those skilled in the relevant art. For example, one feature may be combined with another feature. Therefore, it will be understood that the embodiments shown in the drawings and described above are merely for illustrative purposes, and are not intended to limit the scope of the disclosure, which is defined by the claims that follow as interpreted under the principles of patent law including the doctrine of equivalents.

We claim:

1. A patient support apparatus for supporting a patient, said patient support apparatus comprising:
   a mattress defining a patient support surface, said mattress including an inflatable mattress portion, and said inflatable mattress portion having a plurality of states;
   a control system configured to control inflation or deflation of said inflatable mattress portion to change said state of said inflatable mattress portion between two or more of said plurality of states;
   a user interface in communication with said control system, said user interface configured to allow a user to select an inflate or deflate function of said inflatable mattress portion to change said state of said inflatable mattress portion to a selected state, and said control system being operable to inflate or deflate said inflatable mattress portion in response to said inflate or deflate function being selected at said user interface; and
   said control system configured to generate a notification automatically based on a current state of the inflatable mattress portion, said notification being indicative of said selected state of said inflatable mattress portion to provide a reminder to a caregiver to change said selected state of said inflatable mattress portion.

2. The patient support apparatus according to claim 1, wherein said selected state comprises a deflated state, and said control system generates said notification when said inflatable mattress portion is in said deflated state.

3. The patient support apparatus according to claim 1, said control system comprising a pneumatic system with one or more fluid flow devices to inflate or deflate said inflatable mattress portion.

4. The patient support apparatus according to claim 3, wherein said pneumatic system includes a CPR valve that is actuatable between a closed configuration where flow of air from said inflatable mattress portion is blocked at said CPR valve, and an open position where air can flow from said inflatable mattress portion through said CPR valve.

5. The patient support apparatus according to claim 1, further comprising a light assembly, said light assembly in communication with said control system, and said control system powering said light assembly to generate said notification.

6. The patient support apparatus according to claim 5, wherein said control system intermittently powers said light assembly to generate a flashing light with said light assembly.

7. The patient support apparatus according to claim 1, wherein said user interface comprises a display, said display in communication with said control system and having an icon, and said control system changing said icon at said display to generate said notification.

8. The patient support apparatus according to claim 7, wherein said icon is associated with said mattress.

9. The patient support apparatus according to claim 7, wherein said control system generates a home screen and a notification display window at said display, and said notification display window covers at least a portion of said home screen.

10. The patient support apparatus according to claim 9, wherein said selected state of said inflatable mattress portion is a CPR state wherein said inflatable mattress portion is either fully deflated or max inflated, and wherein said display comprises a touch screen and said notification display window includes an icon at said touch screen, wherein selection of said icon (1) is an acknowledgement by a caregiver to said control system that said inflatable mattress portion is in said CPR state and/or (2) causes said control system to redirect a caregiver to a mattress control template screen where the caregiver can modify said selected state of said inflatable mattress portion.

11. The patient support apparatus of claim 1, wherein said control system is configured to automatically modify said selected state of said inflatable mattress portion in response to (1) a passage of time after said selected state was input into said control system and/or (2) a sensed condition at said mattress.

12. The patient support apparatus according to claim 11, wherein said selected state of said inflatable mattress portion is a CPR state wherein said inflatable mattress portion is either fully deflated or max inflated.

13. The patient support apparatus according to claim 11, wherein said sensed condition at said mattress comprises a characteristic associated with CPR.

14. The patient support apparatus according to claim 13, wherein said characteristic associated with CPR comprises a force associated with CPR, and said control system automatically modifying said selected state when said control system detects a force associated with CPR is no longer present, and further said control system automatically modifying said selected state when said control system detects a force associated with CPR is no longer present after a period of time.

15. The patient support apparatus according to claim 13, wherein said characteristic comprises an increased weight associated with CPR.

16. The patient support apparatus according to claim 15, wherein said control system automatically modifies said selected state when the increased weight is removed.

17. The patient support apparatus according to claim 11, wherein said control system is configured to monitor a biometric condition of a patient supported on said mattress, and said sensed condition at said mattress comprises detecting when the biometric condition of the patient has changed.

18. The patient support apparatus of claim 1, wherein said control system is configured to generate a notification to a device remote from said patient support apparatus.

19. The patient support apparatus according to claim 18, wherein said selected state of said inflatable mattress portion is a CPR state wherein said inflatable mattress portion is either deflated or max inflated.

20. The patient support apparatus according to claim 18, wherein said notification provides a reminder to a caregiver to change said selected state from a treatment state to a pre-treatment state or vice versa.

\* \* \* \* \*